(12) United States Patent
Nagaoka et al.

(10) Patent No.: US 7,847,047 B2
(45) Date of Patent: Dec. 7, 2010

(54) THERMORESPONSIVE POLYMER AND PRODUCTION METHOD THEREOF

(75) Inventors: Hirokazu Nagaoka, Chiba (JP); Noriyuki Ohnishi, Chiba (JP); Masaru Eguchi, Chiba (JP)

(73) Assignee: Chisso Corporation, Osaka (JP)

( * ) Notice: Subject to any disclaimer, the term of this patent is extended or adjusted under 35 U.S.C. 154(b) by 824 days.

(21) Appl. No.: 11/679,493

(22) Filed: Feb. 27, 2007

(65) Prior Publication Data

US 2007/0203313 A1    Aug. 30, 2007

(30) Foreign Application Priority Data

Feb. 28, 2006  (JP)  ............ P.2006-053181
Feb. 23, 2007  (JP)  ............ P.2007-043076

(51) Int. Cl.
*C08F 20/56* (2006.01)
*C08F 120/58* (2006.01)

(52) U.S. Cl. ............ 526/306; 526/303.1; 526/310; 526/312

(58) Field of Classification Search ............ 526/303.1, 526/306, 310, 312
See application file for complete search history.

(56) References Cited

U.S. PATENT DOCUMENTS 5,631,337 A    5/1997   Sassi et al.
5,883,211 A    3/1999   Sassi et al.

FOREIGN PATENT DOCUMENTS

| JP | 04-213311   | * | 8/1992  |
| JP | 2005/082538 |   | 3/2005  |
| WO | 97/40078    |   | 10/1997 |

OTHER PUBLICATIONS

English Language Abstract of JP 2005-082538.
D. Ostrovskii et al, Raman Spectroscopic Characterization of Association and Thermoreversible Gelation in Aqueous Systems of Poly(N-acetamidoacrylamide), Macramolecules 1999, vol. 32, pp. 5552-5560, Aug. 7, 2000.
Howard et al., "Thermally Reversible Homopolymer Gel Systems," Polymer Letters, vol. 2, pp. 1095-1096 (1964).
English translation of JP 4-213311 published Aug. 4, 1992.

* cited by examiner

*Primary Examiner*—Helen L. Pezzuto
(74) *Attorney, Agent, or Firm*—Greenblum & Bernstein, P.L.C.

(57) ABSTRACT

A material which expresses its critical solution temperature even in an aqueous solution containing a buffer or salt, and at the same time, shows small variation width of the critical solution temperature even when concentration of salt or the like contained in water, a buffer liquid or the like is different, interacts with a substance such as a component in the living body and can therefore be used efficiently in the isolation of substances, is provided. A monomer represented by a formula (1) and a thermoresponsive polymer which contains said monomer as a polymerization component.

6 Claims, 1 Drawing Sheet

THERMORESPONSIVE POLYMER AND PRODUCTION METHOD THEREOF

BACKGROUND OF THE INVENTION

1. Field of the Invention

This invention relates to a thermoresponsive polymer, which can change and regulate its polarity and hydrogen bonding performance by changing temperature, and a production method thereof.

2. Background Art

In a compound in which its structure is changed by temperature, pH, light or the like stimulus, its hydrophilic property, hydrophobic property and the like polarities are changed accompanied by its structural changes. A thermoresponsive polymer is known as a compound which causes a structural change by temperature. Illustratively, poly(N-acryloylglycineamide) can be exemplified. This polymer is characterized in that the polymer is dissolved in an aqueous solution when its temperature becomes 38 to 39° C. or more, and the polymer is in-solubilized at 35 to 36° C. or less. This means that it has an upper critical solution temperature (e.g., see Non-patent Reference 1).

[Non-patent Reference 1] Howard C. H. and Norman W. S., *Polymer Letters*, vol. 2 (1964)

However, a polymer having a critical solution temperature has a problem in that the critical solution temperature is apt to change greatly caused by the interfusion of a salt or increase of pH, and the critical solution temperature therefore becomes difficult to be expressed.

In view of the aforementioned present situation, there is a demand for a material which, for example, expresses its critical solution temperature making use of hydrogen bond even in an aqueous solution containing a buffer or salt, and stably shows small variation width of the critical solution temperature, interacts with a substance such as a component in the living body and can therefore be used efficiently in the isolation of the substance of interest.

SUMMARY OF THE INVENTION

The present inventors have found a specific monomer component into which a functional group having hydrogen bonding ability was introduced, further found that a thermoresponsive polymer capable of regulating thermoresponse can be synthesized by polymerizing this, and accomplished the invention based on these findings.

The invention provides the following monomer, thermoresponsive polymer and production method thereof.

[1] A monomer represented by a formula (1):

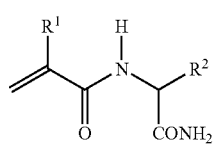

(1)

wherein $R^1$ is hydrogen or methyl, and $R^2$ is carbamoyl, or at least one group selected from the class consisting of methyl, ethyl, propyl, butyl, pentyl, hexyl, cyclopentyl, cyclohexyl, cycloheptyl, methoxy, ethoxy, propoxy, butoxy, pentyloxy and hexyloxy, wherein one or more hydrogen atoms are substituted by carbamoyl.

[2] The monomer described in the aforementioned [1], wherein, in the formula (1), $R^1$ is hydrogen or methyl, and $R^2$ is carbamoyl, methyl wherein one or more hydrogen atoms are substituted by carbamoyl, or ethyl wherein one or more hydrogen atoms are substituted by carbamoyl.

[3] The monomer described in the aforementioned [2], wherein, in the formula (1), $R^1$ is hydrogen, and $R^2$ is —$CH_2$—$CONH_2$ or —$(CH_2)_2$—$CONH_2$.

[4] The monomer described in the aforementioned [2], wherein, in the formula (1), $R^1$ is methyl, and $R^2$ is —$CH_2$—$CONH_2$ or —$(CH_2)_2$—$CONH_2$.

[5] A thermoresponsive polymer obtained by polymerizing the monomer represented by the formula (1) described in anyone of the aforementioned [1] to [4].

[6] A thermoresponsive polymer obtained by polymerizing only the monomer represented by the formula (1) described in anyone of the aforementioned [1] to [4].

[7] The thermoresponsive polymer described in the aforementioned [5] or [6], which has a number average molecular weight of from $10^3$ to $10^6$.

[8] A method for producing the thermoresponsive polymer described in any one of the aforementioned [5] to [7], which comprises treating a polymerization solvent containing a monomer represented by the formula (1) and an initiator with a temperature or light capable of generating a radical from the initiator.

The novel polymer obtained using the novel monomer of the invention shows good thermoresponse and, particularly, exerts an excellent effect of being able to express critical solution temperature even in an aqueous solution containing a buffer or salt. At the same time, since it stably shows small variation width of the critical solution temperature by the difference of properties of water, buffer and the like solutions (e.g., pH, salt concentration and the like), separation operation of a substance such as a component in the living body can be carried out without selecting a solution to be used in the material separation. Because of the possession of this characteristic, the thermoresponsive polymer of the invention can be used efficiently in various applications.

DETAILED DESCRIPTION OF THE INVENTION

Figure 1:
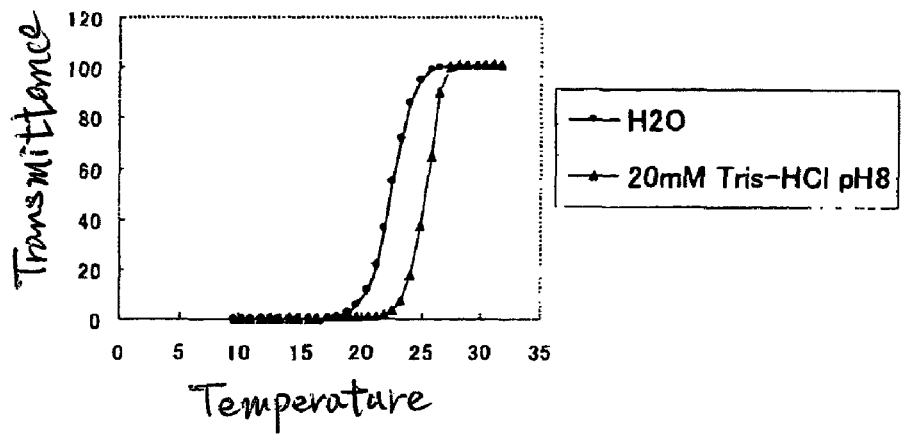
FIG. 1 is a graph showing upper critical solution temperature of the thermoresponsive polymer of the invention obtained in Example 1.

The thermoresponsive polymer of the invention is a thermoresponsive polymer synthesized by introducing a functional group having hydrogen bonding ability into a specified monomer and polymerizing the resulting monomer, which can regulate its critical solution temperature in an aqueous solution.

The term "thermoresponsive polymer" as used herein means a polymer which has a critical solution temperature in an aqueous solution. Also, the term "has upper critical solution temperature" means that it has a characteristic in that when temperature of a solution is lowered, a structural change of the polymer occurs at the critical solution temperature or lower, and the polymer molecules are aggregated. This upper critical solution temperature is referred to as UCST in some cases. The term "has lower critical solution temperature"

means that it has a characteristic in that when temperature of a solution is increased, a structural change of the polymer occurs at the critical solution temperature or higher, and the polymer molecules are aggregated. This lower critical solution temperature is referred to as LCST in some cases. In this connection, a change in polarity can be exemplified as the structural change.

(Monomer to be Used in the Polymerization of Thermoresponsive Polymer)

The thermoresponsive polymer of the invention is characterized in that it is obtained by polymerizing a monomer represented by the following formula (1). The thermoresponsive polymer of the invention is obtained by polymerizing the monomer of the invention as a monomer component. The polymer of the invention may be a thermoresponsive homopolymer obtained by polymerizing this monomer alone, or a thermoresponsive copolymer obtained by copolymerizing this with other monomer component.

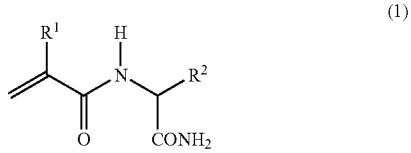

(1)

In the formula (1), $R^1$ is hydrogen or methyl. Also, $R^2$ is carbamoyl, an alkyl wherein one or more hydrogen atoms are substituted with carbamoyl, or an alkoxy wherein one or more hydrogen atoms are substituted with carbamoyl. However, the alkyl in this case is methyl, ethyl, propyl, butyl, pentyl, hexyl, cyclopentyl, cyclohexyl or cycloheptyl, and the alkoxy is methoxy, ethoxy, propoxy, butoxy, pentyloxy, or hexyloxy, which may be linear or branched. Among them, it is preferable that $R^2$ is carbamoyl, methyl wherein one or more hydrogen atoms are substituted by carbamoyl, ethyl wherein one or more hydrogen atoms are substituted by carbamoyl, cyclopentyl wherein one or more hydrogen atoms are substituted by carbamoyl, cyclohexyl wherein one or more hydrogen atoms are substituted by carbamoyl, methoxy wherein one or more hydrogen atoms are substituted by carbamoyl, or ethoxy wherein one or more hydrogen atoms are substituted by carbamoyl, of which carbamoyl, methyl wherein one or more hydrogen atoms are substituted by carbamoyl or ethyl wherein one or more hydrogen atoms are substituted by carbamoyl, are particularly preferable.

A monomer represented by the following formula (2) wherein $R^2$ in the formula (1) is —$CH_2$—$CONH_2$ or a monomer represented by the following formula (3) wherein $R^2$ is —$(CH_2)_2$—$CONH_2$ can be suitably used. Regarding the following formulae (2) and (3), a polymer obtained by polymerizing a monomer wherein $R^1$ is hydrogen and a polymer obtained by polymerizing a monomer wherein $R^1$ is methyl have different physical properties of thermoresponse, so that they can be used by optionally selecting these groups depending on the desired physical property.

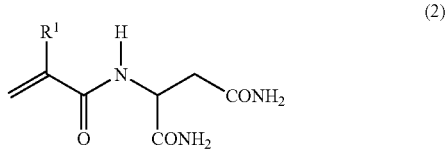

(2)

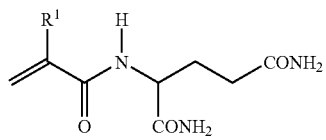

(3)

(Monomer Synthesizing Method)

The monomer represented by the formula (1) can be synthesized from a chloride represented by the following formula (4) and a carbamoyl-containing primary amine compound represented by the following formula (5). As the carbamoyl-containing primary amine compound, asparagineamide hydrochloride, glutamineamide hydrochloride and the like can be exemplified. As the chloride represented by the formula (4), for example, acrylic acid chloride (to be referred sometimes to as acryloyl chloride), methacrylic acid chloride (to be referred sometimes to as methacryloyl chloride) and the like can be used. In addition, acrylic acid anhydride, methacrylic acid anhydride and the like can also be used in the invention, instead of the chloride represented by the formula (4).

Synthesis route of the monomer of the invention represented by the formula (1) is shown in (I). According to this synthesis route (I), the monomer of the invention represented by the formula (1) can be synthesized by allowing the compounds represented by the formulae (4) and (5) to react with each other in the presence of a potassium carbonate aqueous solution and diethyl ether.

Synthesis route (I)

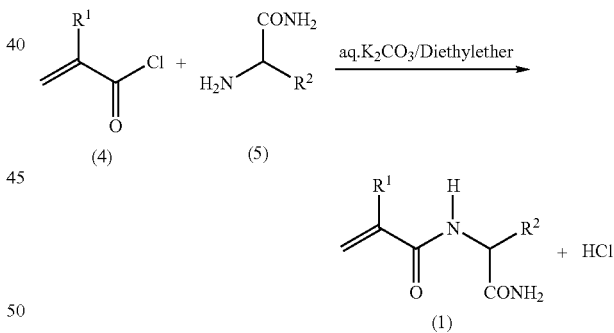

Synthesis example when $R^1$ is hydrogen and $R^2$ is —$CH_2$—$CONH_2$:

Illustratively, as shown in the following synthesis route (II), N-acryloylasparagineamide can be synthesized by allowing acrylic acid chloride and asparagineamide hydrochloride to react with each other in the presence of a potassium carbonate aqueous solution and diethyl ether.

Synthesis example when $R^1$ is methyl and $R^2$ is —$CH_2$—$CONH_2$:

N-methacryloylasparagineamide can be synthesized by allowing methacrylic acid chloride and asparagineamide hydrochloride to react with each other in the presence of a potassium carbonate aqueous solution and diethyl ether.

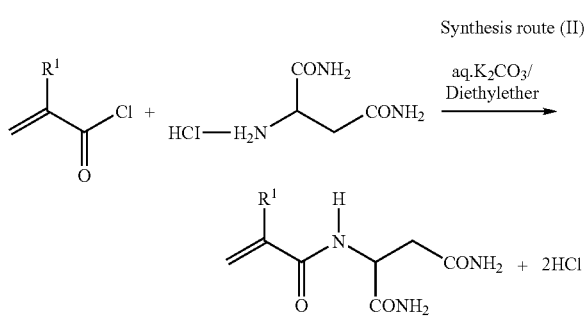

Synthesis route (II)

Synthesis example when $R^1$ is hydrogen and $R^2$ is $—(CH_2)_2—CONH_2$:

Also, as shown in the following synthesis route (III), N-acryloylglutamineamide can be synthesized by allowing acrylic acid chloride and glutamineamide hydrochloride to react with each other in the presence of a potassium carbonate aqueous solution and diethyl ether.

Synthesis example when $R^1$ is methyl and $R^2$ is $—(CH_2)_2—CONH_2$:

N-methacryloylglutamineamide can be synthesized by allowing methacrylic acid chloride and glutamineamide hydrochloride to react with each other in the presence of a potassium carbonate aqueous solution and diethyl ether.

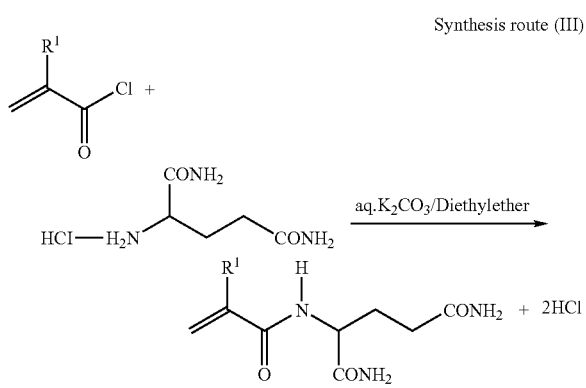

Synthesis route (III)

The thermoresponsive polymer of the invention may be a homopolymer which comprises a monomer represented by the aforementioned formula (1) as a monomer component, or a copolymer of this with other monomer. As the other copolymerizable monomer component, methacrylamide, acrylamide, N-acryloylglycineamide and the like can be exemplified. Content of the monomer represented by the formula (1) in these copolymers is not particularly limited, but is preferably 50% by mass or more, more preferably 90% by mass or more.

Molecular weight of the thermoresponsive polymer is not particularly limited, but a number average molecular weight of from $10^3$ to $10^6$, preferably from $10^3$ to $10^5$, can be employed.

(Production Method of Thermoresponsive Polymer)

The thermoresponsive polymer of the invention can be produced, for example, by the method shown below.

The monomer to be used as the raw material of the polymer and an initiator are dissolved in a polymerization solvent, and the polymerization reaction is started by heating or the like. When a chain transfer agent is dissolved in the polymerization solvent in this case, molecular weight of the obtained polymer can be adjusted, and a reactive functional group can be further introduced into the terminal of the obtained polymer. After the polymerization reaction, the thermoresponsive polymer of interest can be purified by carrying out dialysis of the polymer-containing solution to remove unreacted monomer and low molecular weight thermoresponsive polymers and the like unnecessary low molecular weight polymers, or by carrying out reprecipitation of the polymer in a poor solvent.

A functional group such as carboxyl group, hydroxyl group, amino group, cyano group or a straight or branched chain alkyl group having from 1 to 20 carbon atoms may be optionally introduced into the polymer chain terminus of the thermoresponsive polymer of the invention. Since introduction of these functional groups renders possible provision of various functions, this is advantageous when, for example, immobilized on magnetic fine particles. As the method for introducing a functional group, any conventionally known method can be employed optionally. In this case, a chain transfer agent and an initiator may be used if necessary. As the chain transfer agent, mercaptopropionic acid, aminoethanethiol, butanethiol or the like compound containing a functional group having from 1 to 20 carbon atoms can for example be used. Also, a compound having amino group or carboxyl group can be used as the initiator.

According to the invention, temperature range of the critical solution temperature (switching range) is not particularly limited, but is preferably as narrow as possible in view of practical use. The temperature range is generally 10° C. or less, preferably from 0 to 7° C., more preferably from 0 to 5° C.

Figure 2:
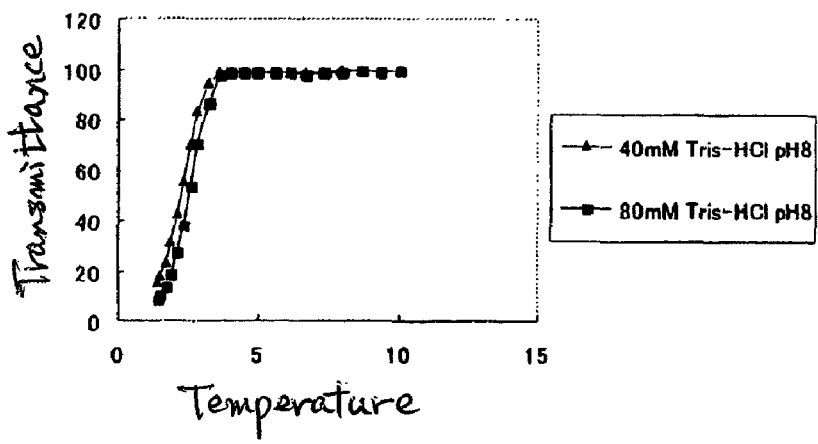
FIG. 2 is a graph showing upper critical solution temperature of the thermoresponsive polymer of the invention obtained in Example 2.
Figure 3:
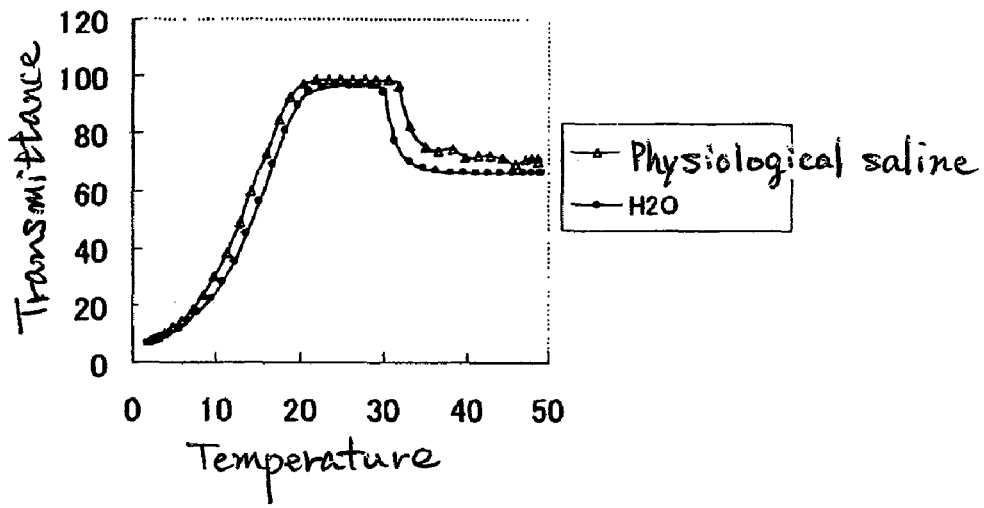
FIG. 3 is a graph showing upper critical solution temperature and lower critical solution temperature of the thermoresponsive polymer of the invention obtained in Example 3.

FIG. 1 is a graph showing upper critical solution temperature of the thermoresponsive polymer of the invention obtained in Example 1. This is a graph prepared by dissolving the polymer in deionized water and a buffer liquid, measuring temperature (° C.) of respective solutions and transmittance of the solutions at each temperature, and plotting the values. FIG. 2 is a graph showing upper critical solution temperature of the thermoresponsive polymer of the invention obtained in Example 2. This is a graph prepared by dissolving the polymer in a buffer liquid having different concentrations, measuring temperature (° C.) of respective solutions and transmittance of the solutions at each temperature, and plotting the values. FIG. 3 is a graph showing upper critical solution temperature and lower critical solution temperature of the thermoresponsive polymer of the invention obtained in Example 3. This is a graph prepared by dissolving the polymer in deionized water and physiological saline, measuring temperature (° C.) of respective solutions and transmittance of the solutions at each temperature, and plotting the values. In the FIG. 1 to FIG. 3, the upper critical solution temperature represents a temperature when a transmittance is 50%, and the lower critical solution temperature represents a temperature when a transmittance is 80%.

EXAMPLES

The following describes the invention further in detail based on examples, but the invention is not restricted thereby. In this connection, the terms and measuring methods of physical properties are as follows.

(NMR Analysis)

Structure of each polymer was confirmed by 400 MHz 1H-NMR (mfd. by JEOL). Heavy water was used as the measuring solvent of NMR.

(Molecular Weight Measurement by GPC)

Molecular weight was determined by GPC (main body: Shimadzu Corp., column: G 4000 PW (TOSOH)) using 0.1 M $NaNO_3$ as the eluting solvent.

(Measurement of Critical Solution Temperature)

Upper critical solution temperature and lower critical solution temperature were measured using transmittance of visible light (550 nm). The measuring temperature was lowered or increased at a rate of 1° C./min.

Example 1

(Synthesis of N-acryloylasparagineamide)

A 5 ml portion of acrylic acid chloride and 200 ml of diethyl ether were put into a 500 ml capacity eggplant type flask and stirred on an ice bath. Next, 1.84 g of asparagineamide hydrochloride (mfd. by Kokusan Kagaku) was dissolved in 40 ml of deionized water, and 3 g of potassium carbonate was dissolved in 20 ml of deionized water. The asparagineamide aqueous solution was mixed with the potassium carbonate aqueous solution. The mixed liquid was added dropwise into the eggplant type flask spending 10 minutes while stirring constantly, and the mixture after completion of the dropwise addition was stirred for 24 hours. Diethyl ether layer in the thus obtained reaction liquid was discarded, and the water layer was concentrated at 25° C. under a reduced pressure. One liter of acetone was added to the thus obtained residue and stirred for 1 hour. The insoluble solids were removed by suction filtration. By recrystallizing from the acetone layer, 0.5 g of colorless crystals were obtained.

The thus obtained crystals showed a characteristic of the compound of interest by the NMR analysis.

$^1$H-NMR (in $d_2O$) $CH_2$: 2 H, multi, δ 2.75-2.58, CH: 1 H, multi, δ 4.68-4.60, CH: 1 H, multi, δ 5.68-5.65, $CH_2$: 2 H, multi, δ 6.20-6.07.

(Synthesis of N-acryloylasparagineamide Polymer)

In an atmosphere of nitrogen, 50 mg of N-acryloylasparagineamide, 10 μl of TEMED (N,N,N',N'-Tetramethyl ethylenediamine) and 10 mg of APS (Ammonium Peroxodisulfate) were dissolved in 25 ml of deionized water, put into a 100 ml capacity flask and stirred at 40° C. for 4 hours. This reaction liquid was dialyzed against 3 liters of deionized water for 24 hours using a dialysis tube, and the unreacted matter was removed. When the dialyzed liquid was freeze-dried and then the polymer was dissolved in deionized water to a concentration of 0.2% (w/v) to verify its thermoresponse, it showed the upper critical solution temperature at 22° C., and when dissolved in a buffer liquid (composition: 20 mM Tris-HCl pH 8) to a concentration of 0.2% (w/v) and its thermoresponse was verified, it was found that it shows the upper critical solution temperature at 25° C. It was found from this that the temperature showing the upper critical solution temperature of the thus obtained polymer hardly undergoes influences of salt concentration and the like in the solution. Number average molecular weight of the thus obtained polymer of N-acryloylasparagineamide was 16,000.

Example 2

(Synthesis of N-acryloylglutamineamide)

A 5 ml portion of acrylic acid chloride and 200 ml of diethyl ether were put into a 500 ml capacity eggplant type flask and stirred on an ice bath. Next, 2 g of glutamineamide hydrochloride (mfd. by Kokusan Kagaku) was dissolved in 25 ml of deionized water, and 3 g of potassium carbonate was dissolved in 25 ml of deionized water. The glutamineamide aqueous solution was mixed with the potassium carbonate aqueous solution. The mixed liquid was added dropwise into the eggplant type flask spending 10 minutes while stirring constantly, and the mixture after completion of the dropwise addition was stirred for 24 hours. Diethyl ether layer in the thus obtained reaction liquid was discarded, and the water layer was concentrated at 25° C. under a reduced pressure. A 500 ml portion of acetone was added to the thus obtained residue and stirred for 1 hour. The insoluble solids were removed by suction filtration. By recrystallizing from the acetone layer, 0.25 g of colorless crystals were obtained.

The thus obtained crystals showed a characteristic of the compound of interest by the NMR analysis.

$^1$H-NMR (in $d_2O$) $CH_2$: 2 H, multi, δ 2.09-1.84, $CH_2$: 2 H, t, δ 2.29-2.25, CH: 1 H, multi, δ 4.25-4.22, CH: 1 H, d, δ 5.70-5.68, $CH_2$: 2 H, multi, δ 6.23-6.09.

(Synthesis of N-acryloylglutamineamide Polymer)

In an atmosphere of nitrogen, 50 mg of N-acryloylglutamineamide, 10 μl of TEMED and 10 mg of APS were dissolved in 25 ml of deionized water, put into a 100 ml capacity flask and stirred at 30° C. for 4 hours. This reaction liquid was dialyzed against 3 liters of deionized water for 24 hours using a dialysis tube, and the unreacted matter was removed. When the dialyzed liquid was freeze-dried and then the polymer was dissolved in a buffer liquid (composition: 40 mM Tris-HCl pH 8) to a concentration of 0.2% (w/v) to verify its thermoresponse, it showed the upper critical solution temperature at 2° C., and when dissolved in a buffer liquid (composition: 80 mM Tris-HCl pH 8) and its thermoresponse was verified, it was found that it shows the upper critical solution temperature at 3° C. It was found from this that the temperature showing the upper critical solution temperature of the thus obtained polymer hardly undergoes influences of salt concentration and the like in the solution. Number average molecular weight of the thus obtained polymer of N-acryloylglutamineamide was 17,000.

Example 3

(Synthesis of N-methacryloylasparagineamide)

A 11.3 ml portion of methacrylic acid chloride, 1 g of asparagineamide hydrochloride (mfd. by Kokusan Kagaku) and 50 ml of diethyl ether were put into a 300 ml capacity eggplant type flask and stirred on an ice bath. Next, 20 ml of saturated potassium carbonate aqueous solution was added dropwise thereto. Thereafter, this was stirred on an ice bath for 30 minutes and then at room temperature for 12 hours. Diethyl ether layer in the thus obtained reaction liquid was discarded, and the water layer was dissolved in 100 ml of methanol. After filtration, the filtrate was concentrated under a reduced pressure and fractionated by a silica gel column using methanol as the developing solvent. The thus obtained amide compound fraction was purified using an ion exchange resin ("Dynaion (trade name) PA 412" mfd. by Mitsubishi Kagaku) After concentration under a reduced pressure and subsequent drying under a reduced pressure, 0.43 g of colorless crystals were obtained.

The thus obtained crystals showed a characteristic of the compound of interest by the NMR analysis.

$^1$H-NMR (in $d_2O$) $CH_3$: 3 H, s, δ 1.82, $CH_2$: 2 H, multi, δ 2.78-2.61, CH: 1 H, multi, δ 4.65-4.57, CH: 1 H, s, δ 5.40, CH: 1 H, s, δ 5.62.

(Synthesis of N-methacryloylasparagineamide Polymer)

In an atmosphere of nitrogen, 50 mg of N-methacryloylasparagineamide, 10 µl of TEMED and 10 mg of APS were dissolved in 25 ml of deionized water, put into a flask and stirred at 50° C. for 1 hour to effect polymerization. This reaction liquid was dialyzed against 3 liters of deionized water for 24 hours using a dialysis tube, and the unreacted matter was removed. When the dialyzed liquid was freeze-dried and then the polymer was dissolved in deionized water to a concentration of 0.2% (w/v) to verify its thermoresponse, it showed the upper critical solution temperature at 13° C., and showed the lower critical solution temperature at 33° C. When the polymer was dissolved in physiological saline to a concentration of 0.2% (w/v), it showed the upper critical solution temperature at 13° C., and showed the lower critical solution temperature at 30° C. It was found from this that the temperature showing the upper critical solution temperature and lower critical solution temperature of the thus obtained polymer hardly undergoes influences of salt concentration in the solution. Number average molecular weight of the thus obtained polymer of N-methacryloylasparagineamide was 22,000.

Since the polymer of the invention is a novel thermoresponsive polymer having good thermoresponse, it can be applied to an adsorption separation material, a substance releasing material, a bio-function material and the like, making use of the changes in polarity and hydrogen bonding performance by temperature. Illustratively, it can be suitably applied to thermoresponsive magnetic fine particles and the like. The thermoresponsive magnetic fine particles are those in which a thermoresponsive polymer is immobilized on magnetic fine particles, wherein size of the particles changes by a change of temperature, and the thermoresponsive polymer of the invention can be used, for example, as the stimulus responding polymer of magnetic fine particles described in JP-A-2005-82538.

This application is based on Japanese patent applications JP 2006-053181, filed on Feb. 28, 2006, and JP 2007-043076, filed on Feb. 23, 2007, the entire content of which is hereby incorporated by reference, the same as if set forth at length.

What is claimed is:

1. A thermoresponsive polymer obtained by polymerizing the monomer represented by a formula (1)

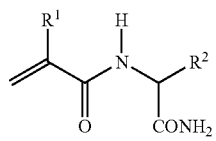

(1)

wherein $R^1$ is hydrogen or methyl, wherein when $R^1$ is hydrogen, $R^2$ is carbamoyl, or at least one group selected from the class consisting of methyl, ethyl, propyl, butyl, pentyl, hexyl, cyclopentyl, cyclohexyl, cycloheptyl, methoxy, ethoxy, propoxy, butoxy, pentyloxy and hexyloxy, wherein one or more hydrogen atoms are substituted by carbamoyl; or wherein when $R^1$ is methyl, $R^2$ is carbamoyl, or at least one group selected from the class consisting of methyl, propyl, butyl, pentyl, hexyl, cyclopentyl, cyclohexyl, cycloheptyl, methoxy, ethoxy, propoxy, butoxy, pentyloxy and hexyloxy, wherein one or more hydrogen atoms are substituted by carbamoyl.

2. A thermoresponsive polymer obtained by polymerizing only the monomer represented by a formula (1)

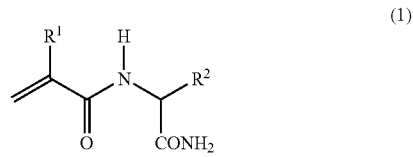

(1)

wherein $R^1$ is hydrogen or methyl, and $R^2$ is carbamoyl, or at least one group selected from the class consisting of methyl, ethyl, propyl, butyl, pentyl, hexyl, cyclopentyl, cyclohexyl, cycloheptyl, methoxy, ethoxy, propoxy, butoxy, pentyloxy and hexyloxy, wherein one or more hydrogen atoms are substituted by carbamoyl.

3. The thermoresponsive polymer described in claim 1, which has a number average molecular weight of from $10^3$ to $10^6$.

4. The thermoresponsive polymer described in claim 2, which has a number average molecular weight of from $10^3$ to $10^6$.

5. A method for producing the thermoresponsive polymer described in claim 1, which comprises treating a polymerization solvent containing a monomer represented by the formula (1) and an initiator with a temperature or light capable of generating a radical from the initiator to perform a polymerization.

6. A method for producing the thermoresponsive polymer described in claim 2, which comprises treating a polymerization solvent containing a monomer represented by the formula (1) and an initiator with a temperature or light capable of generating a radical from the initiator to perform a polymerization.

* * * * *